(12) United States Patent
Taylor et al.

(10) Patent No.: US 10,436,690 B2
(45) Date of Patent: Oct. 8, 2019

(54) GLOVE IMPACT RESISTANCE TESTING (71) Applicant: Wells Lamont Industrial Group LLC, Niles, IL (US)

(72) Inventors: Dalia Taylor, Midlothian, VA (US); William Trainer, Niles, IL (US); Andrew Funk, Niles, IL (US); Angela Fisher, Tomahawk, WI (US)

(73) Assignee: WELLS LAMONT INDUSTRY GROUP LLC, Skokie, IL (US)

( * ) Notice: Subject to any disclaimer, the term of this patent is extended or adjusted under 35 U.S.C. 154(b) by 95 days.

(21) Appl. No.: 15/632,800

(22) Filed: Jun. 26, 2017

(65) Prior Publication Data

US 2017/0370815 A1    Dec. 28, 2017

Related U.S. Application Data (60) Provisional application No. 62/354,419, filed on Jun. 24, 2016.

(51) Int. Cl.
*G01N 3/303* (2006.01)
*A41D 19/015* (2006.01)
(Continued)

(52) U.S. Cl.
CPC ....... *G01N 3/303* (2013.01); *A41D 19/01523* (2013.01); *G01L 5/0052* (2013.01); *G01N 3/30* (2013.01)

(58) Field of Classification Search
None
See application file for complete search history.

(56) References Cited

U.S. PATENT DOCUMENTS 7,174,257 B2 *  2/2007  Wright .................. G01L 5/0038
                                                               702/41
7,254,840 B2 *  8/2007  Hammons ........ A41D 19/01523
                                                                 2/16
(Continued)

FOREIGN PATENT DOCUMENTS

DE   10325958 A1 *  12/2004  ............... G01N 3/28
DE   10325958 A1    12/2004
(Continued)

OTHER PUBLICATIONS

ASTM International Designation: D2632-01; Standard Test Method for Rubber Property—Resilience by Vertical Rebound1; p. 1-5 (Year: 2012).*

(Continued)

*Primary Examiner* — Peter J Macchiarolo
*Assistant Examiner* — Jermaine L Jenkins
(74) *Attorney, Agent, or Firm* — Levenfeld Pearlstein, LLC (57) ABSTRACT

An impact resistance test method of a glove having a protective material includes applying an impact force, with an impactor, to the glove at a plurality of locations on a section of the glove, measuring, with a load cell, a transferred impact force transferred through the section of the glove, and determining an impact resistance of the glove based on the measured transferred impact force. The impactor has a predetermined weight and is dropped from a predetermined height to apply the impact force to the section of the glove. An apparatus for carrying out the test method is also provided.

12 Claims, 3 Drawing Sheets

(51) Int. Cl.
  *G01L 5/00* (2006.01)
  *G01N 3/30* (2006.01)

(56) References Cited

U.S. PATENT DOCUMENTS

| | | | | |
|---|---|---|---|---|
| 8,221,291 | B1* | 7/2012 | Kantarevic | G06F 19/3481 |
| | | | | 482/8 |
| 8,572,764 | B2* | 11/2013 | Thellmann | A63B 21/4033 |
| | | | | 2/161.1 |
| 9,962,593 | B1* | 5/2018 | Massner | G04F 10/00 |
| 2009/0113592 | A1* | 5/2009 | Iwata | A41D 19/01523 |
| | | | | 2/19 |
| 2014/0343701 | A1* | 11/2014 | Song | A63B 71/06 |
| | | | | 700/92 |

FOREIGN PATENT DOCUMENTS

| | | | |
|---|---|---|---|
| WO | 2007007211 | A2 | 1/2007 |
| WO | 2015077044 | A1 | 5/2015 |

OTHER PUBLICATIONS

International Search Report issued by ISA/EPO in connection with PCT/US2017/039225 dated Oct. 25, 2017.
International Preliminary Report on Patentability issued by IB in connection with PCT/US2017/039225 dated Jan. 3, 2019.
Written Opinion issued by ISA/EPO in connection with PCT/US2017/039225 dated Jan. 3, 2019.

* cited by examiner

| Samples | Location on Hand Tested Force Applied To: | Location Where Force was Applied Notes | Transferred Impact Force Individual Readings (lbs Force) | Transferred Impact Force (lbs) | Transferred Impact Force (lbs): Overall BOH | % Impact Resistance | % Impact Resistance (average) | Impact Protection, Cover Factor: Back of Hand, Knuckle, Fingers and Thumb | Impact Protection, Cover Factor: Overall BOH |
|---|---|---|---|---|---|---|---|---|---|
| | Back of Hand | lower left corner | 31.70 | 35.9 | | 78.9% | 62.5% | 85% | 88% |
| | | center | 33.15 | | | | | | |
| | | upper right corner | 42.75 | | | | | | |
| 12459 | Knuckle Strap | left side of knuckle strap | 29.33 | 55.4 | 64 | 67.4% | | 85% | |
| | | center | 29.39 | | | | | | |
| | | right side of knuckle | 107.53 | | | | | | |
| | Finger | bottom, middle finger | 41.17 | 92.3 | | 45.7% | | 85% | |
| | | knuckle, middle finger | 119.07 | | | | | | |
| | | finger tip, middle finger | 116.52 | | | | | | |
| | Thumb | lower thumb | 38.80 | 71.2 | | 58.1% | | 95% | |
| | | knuckle, thumb | 66.12 | | | | | | |
| | | thumb finger tip | 108.75 | | | | | | |

GLOVE IMPACT RESISTANCE TESTING

BACKGROUND

The following description relates generally to a method for testing impact resistance of a glove, and an apparatus for performing such a test.

A human hand includes a number of bones, major nerves, arteries, veins, muscles, tendons, ligaments, joint cartilage, skin and fingernails. Worksite injuries to hands sometimes include injuries to one or more of the hand parts listed above. Such injuries may require medical attention which may result in worker and/or worksite downtime as well as large healthcare and/or insurance costs.

Impact-resistant gloves have been developed in an effort to reduce hand injuries. Impact-resistant gloves typically include high density thermoplastic rubber pads or overlays positioned along a top or back side of the glove, corresponding to a back of a wearer's hand, and along fingers to protect from impacts. Some impact-resistant gloves may also include padded palms, molded knuckle areas and extra grip patches.

Standard testing protocols have been developed by organizations, such as the American Society for Testing and Materials ("ASTM"), for testing impact resistance of various products. Following such standardized procedures, impact resistance may be compared across different products. One such testing standard is ASTM 1446-12. Under ASTM 1446-12, performance characteristics of a protective headgear may be evaluated. ASTM 1446-12 requires a mass, approximately 3 to 6 kg to be dropped and impact attenuation is measured. An impactor is secured with the protective material or head gear.

Another standard, ASTM F1937-04, provides a standard specification for body protectors used in horse sports and for horseback riders. In ASTM F1937-04, a 0.5 meter drop of a mass creates an impact velocity of 10.33 feet per second (ft/s). The peak acceleration (impact attenuation) of any impact shall not exceed 300 g. The inbound velocity, $g_{max}$ (maximum acceleration) and deformation depth are recorded for each impact.

Still another standard, ASTM F2412-11, relates to standard test methods for foot protection. In ASTM F2412-11, a 22.7 kg mass is dropped onto a wax form to create an impact of 75 ft-lb. A distance from a lowest point in an impression made in the wax form is measured.

Another standard, EN (European Standard) 13594, relates to protective gloves for motorcyclists. Under EN 13594, in order to pass the test, a transmitted impact force through a test glove cannot exceed 4 kN (900 lbs) after being impacted by 5 J (3.7 ft-lb) of energy.

Another test for determining impact protection is described in the EN 1621-1 standard. The EN 1621-1 standard relates to a test for determining impact resistance of protective motorcycle armor. In EN 1621-1, a piece of motorcycle armor is disposed on a 50 mm radius hemispherical dome or anvil mounted on a load cell. A 5 kg mass with an 80 mm×40 mm flat striking face is dropped from a height sufficient to create an impact energy of 50 J onto the armor. The force transmitted through the armor is measured by the load cell. A mean maximum transmitted force is not to exceed 35 kN in order to pass the test, and no single value should exceed 50 kN.

Another test is commonly referred to as the "wood block test." In the wood block test, a test object is placed on one or more wood blocks. The test object may be an intact glove or a back of the glove split from the palm. The wood blocks are supported at their ends and extend across a gap. A mass is dropped onto the sample, imparting a force that is transferred to the wood blocks. If a sufficiently large force is transferred to the wood blocks, the blocks will fail. This may occur in situations where the sample does not have adequate impact protection. When the sample includes adequate protection, the wood blocks may remain intact after application of the impact force.

However, neither ASTM nor the European standards provide a test for measuring a reduction in hand impact force. In addition, none of the standard test protocols described above, or other similar test protocols, use a weight suitable for testing impact resistance or protection on a back of a glove, as the weights or masses involved in the tests above exceed weights or masses that could cause hand injuries if applied to a glove in a work environment scenario. That is, in the tests described above, the energy imparted on the glove or other test object (e.g., motorcycle armor or head gear) is higher than that which typically causes hand injuries. As such, these tests do not test gloves at a practical level of force where hand injuries may be avoided or mitigated.

Further, in the above tests, the striking face of the mass or impactor is unsuitably large for simulating impacts that are imparted on work gloves during use in work environments. That is, in the tests above, a striking face may be so large that the impact is distributed across a large surface of glove. As such, impact resistance of smaller, particular sections of the glove, for example, those sections corresponding to joints of the hand or knuckles, cannot be accurately determined. Other tests, such as the wood block test, are not scientific and may not be reliably repeated to obtain consistent quantitative data or accurate comparisons between test objects.

Some glove manufacturers have developed other tests, or use portions of standard tests, in an effort to determine or measure impact resistance. For example, in one test, carrots are inserted into a glove as a substitute for fingers. A 3.5 lb pipe is dropped onto the glove from approximately 16 inches. However, this test is suitable for demonstration purposes only, and lacks scientific value. For example, such a test cannot be reliably repeated and results cannot be reliably reproduced. In addition, carrots are poor models for human fingers. This test may also refer to ASTM D2632, which is a vertical rebound test that is not directly applicable to impact protection. That is, ASTM D2632 is not scientific for testing resistance to impact. Rather, ASTM D2632 compares the viscoelastic or bounce-back properties of materials.

Another test is a combination of the wood block test described above and the EN 1621-1 test. In such a test, a glove is placed either intact or split back from the palm on a load cell. A mass is dropped on the glove and the load is measured at the load cell via a computer interface, under EN 1621-1. However, as discussed above, the wood block test is not scientific and results are difficult to reproduce.

In still another test, a glove is mounted on a mandrel and a mass is released onto the glove and mandrel with a toggle. The test may use a twin rail design for movement of the mass and results may appear on a dial, also supported by the twin rail. However, in such a test, use of the mandrel does not allow for a wide range of testing at different locations on the back of the glove. In addition, the dial readout may be inaccurate.

In still another test, a glove is placed intact, or possibly filled with a ballistics gel, on a support surface. A weight block with a mandrel is released from a specified height and the impact force is measured by a load cell. However, in this test, measuring the load of an intact glove measures the impact resistance of both the back of the glove and the palm of the glove, and in some cases, the ballistics gel. Thus, the load cell measurement is not a measurement of impact resistance at the back of the glove alone.

Other impact tests, as well as those above, do not take into consideration or measure a precise impact resistance of the glove at specific points of impact.

Accordingly, it is desirable to provide an impact resistance testing method suitable for measuring a transmitted impact force (i.e., impact resistance) through a glove at at least one location, and preferably, at each of a plurality of locations. It is also an object to provide an apparatus for performing such a test.

SUMMARY

According to one embodiment, there is provided an impact resistance test method of a glove having a protective material. The method includes applying an impact force, with an impactor, to the glove at a plurality of locations on the glove, measuring, with a load cell, a transferred impact force transferred through the glove, and determining an impact resistance of the glove based on the measured transferred impact force. The impactor has a predetermined weight and is dropped from a predetermined height to apply the impact force to the glove.

According to another embodiment, there is provided an apparatus for performing an impact resistance test method on a glove. The apparatus includes a frame, an impactor configured for vertical movement to impact the glove, an impactor guide configured to hold the impactor at a first position, release the impactor, and guide the impactor during vertical movement, a support surface configured to support the glove, wherein the support surface is substantially flat, a load cell operably connected to the support surface, the load cell configured to measure a transferred impact force transferred through the glove, and a control system operably and communicably connected to the load cell, the control system configured to receive the measured transferred impact force from the load cell and determine an impact resistance of the glove based on the measured transferred impact force and a baseline impact transferred force.

The present method and apparatus can be used to test the impact protection of the fingers as well, whereas prior methods and devices could only be used to test impact protection of the back of the hand/glove.

These and other features and advantages of the present invention will be apparent from the following detailed description, in conjunction with the appended claims.

BRIEF DESCRIPTION OF THE DRAWINGS

FIGS. 3A and 3B show an embodiment of an impact resistance testing apparatus, in which

DETAILED DESCRIPTION

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

A method for testing and determining impact resistance of a glove and an apparatus for carrying out the test are described herein. Generally, the method includes applying an impact force (also referred to herein as the "applied impact force") to a test object, such as a glove, and measuring an impact force transferred through the test object (also referred to herein as the "transferred impact force"). From this, it can be determined how much of the applied impact force was absorbed or dissipated by the test object. In one embodiment, the applied impact force may be applied, individually, to a plurality of locations on the test object.

The applied impact force may be provided by dropping an impactor having predetermined mass or weight, over a predetermined distance or height, onto the test object. In another embodiment, the impactor is dropped under the force of gravity alone. In another embodiment, the impactor may be driven onto the test object. In one embodiment, the predetermined weight may be approximately 1 lb, and the predetermined distance or height may be approximately 6 inches. Other weights and distances are envisioned, however.

The test object may be disposed on a support surface that is operably connected to a load cell. The load cell is configured to measure a transferred impact force through the test object in response to striking the test object with the impactor. A baseline maximum transferred impact force may be determined by carrying out the test method on a test object with no protective material (i.e., no impact resistant material or padding). Subsequently, a transferred impact force measured on a test object having protective material and tested according to the embodiments described herein, can be compared to the baseline maximum transferred impact force to obtain a percentage of impact resistance. It is understood that the predetermined weights and distances may be varied. However, to accurately compare results across different test objects, the predetermined weights and distances should remain constant across the tests with different test objects.

Figure 1:
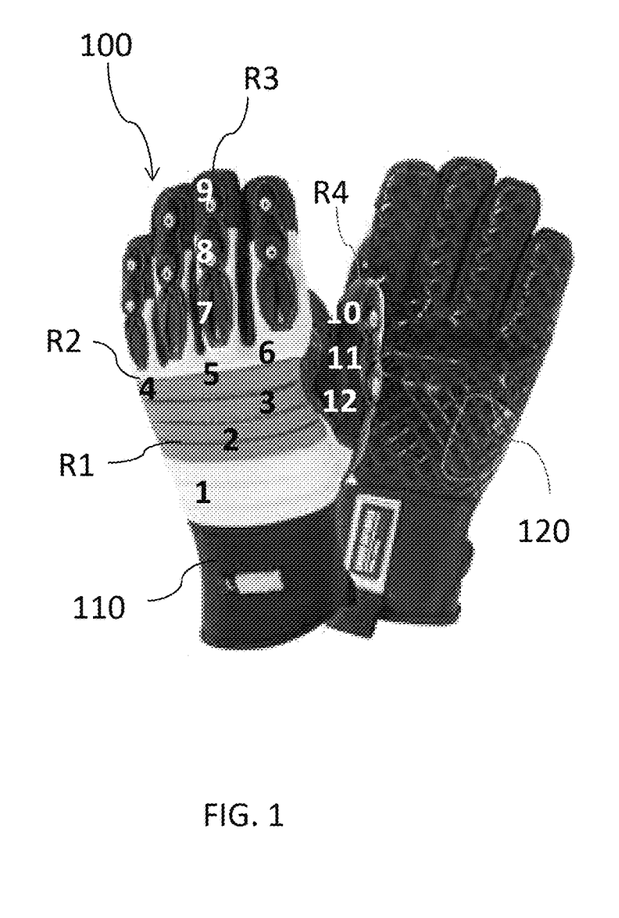
FIG. 1 is a perspective view showing a back side and a front side of an impact resistant glove, including a plurality of locations for applying an impact force in an impact resistance test, according to one embodiment.

FIG. 1 shows a pair of gloves 100, according to an embodiment described herein, which may be used as the test object. In one embodiment, the test object is a back side 110 of a glove 100, i.e., the surface of a glove configured to cover the back side (opposite to the palm side) of the wearer's hand. The glove 100 preferably includes a protective material on the back side. The protective material may be disposed on the back side 110 of the glove 100 in any suitable manner to increase protection of a wearer's hand from impact forces, and is included in the glove in addition to material from which a body of the glove is constructed. In one embodiment, the protective material may be disposed along areas of the glove that generally correspond to fingers, knuckles, and/or a backside of the hand.

The protective material may be applied in layers or in spaced segments to allow for flexibility of the glove. The protective material is configured to absorb or dissipate energy imparted to the glove so as to reduce impact to a wearer's hand. The protective material may function as padding to the wearer's hand and may include, for example, a thermoplastic elastomer, such as thermoplastic rubber or other similar material that is suitably soft, stretchy and has the elastic properties of rubber. Another suitable protective material is D30, which is based on a non-Newtonian material that behaves differently depending on the force applied. Such a material, sometimes referred to as a shear-thickening or thixotropic fluid, behaves like a solid when encountering mechanical stress or shear. Still another suitable protective material is XRD, which is a Poron microcellular urethane. XRD is soft while at rest above the glass transition temperature of the urethane molecules. When stressed at a high rate or impacted quickly, the glass transition temperature of the material reaches a point where the urethane momentarily "freezes." Yet another suitable protective material is foam, such as a polyurethane or polyethylene foam. Foam traps pockets of air in a solid such as rubber or polystyrene. Other suitable protect materials are envisioned as well.

In one embodiment, the test may be performed to a section of the glove 100. For example, the section may be a back side 110 of the glove that has been cut away or separated from a front or palm side 120 of the glove 100 to carry out the test method. Accordingly, impact resistant characteristics of the front side 120 of glove may be avoided when measuring the transferred impact force. In another embodiment, the test object may be, for example, the protective material by itself.

The present disclosure is not limited to the embodiments above, however. For example, the test methods described herein may be carried out on a front or palm side of a glove as well. Such a test may be particularly useful when the palm side of the glove is provided with a protective material designed to provide impact resistance.

Referring to FIG. 1, in one embodiment, the test method includes applying the impact force at a plurality of locations 1-12 on the back side 110 of the glove 100. For example, the impact force may be applied at multiple locations on the glove 100 within specific regions R1, R2, R3, R4 corresponding to positions on a wearer's hand, such as the center of the back of the hand R1, the knuckles R2, the index finger R3 and the thumb R4. In one embodiment, the impact force may be applied multiple times at one or more of the locations as part of the method. Although FIG. 1 illustrates twelve locations for applying the impact force, it is understood that additional or fewer locations may be selected. In addition, testing may be carried out in additional or fewer regions on the glove.

Figure 2:
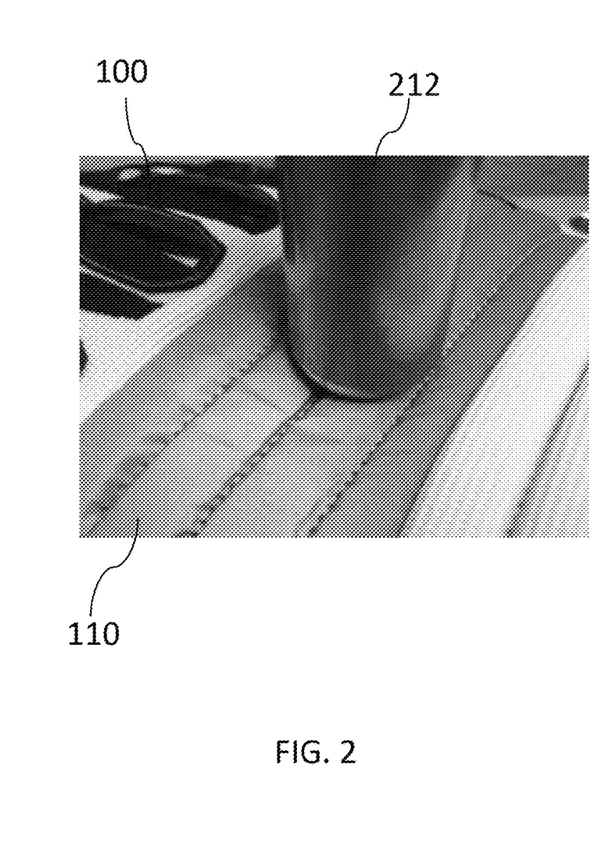
FIG. 2 is an enlarged view of a portion of the back side of the glove in FIG. 1 during an impact resistance test at a location on the glove, according to one embodiment.

FIG. 2 shows an example of an impact force being applied to a back side 110 of a glove 100 by an impactor 212 (described further below with reference to FIGS. 3A and 3B), according to one embodiment. As shown in FIG. 2, the impact force is applied to a location on the glove 100 having an area that is significantly less than an entire area of the glove 100. Accordingly, impact resistance may be determined at a plurality of locations and/or regions on the glove according to the embodiment described herein.

In the test methods described herein, it may be useful to determine, for example, an average impact resistance over the protected area on a glove, and the average impact resistance coverage present on different glove styles or models. That is, the impact resistance test of the present disclosure may be carried out on different glove styles. Accordingly, a suitable comparison of impact resistance across different glove styles may be obtained.

In one embodiment, the support surface may be a substantially flat surface on which the test object, such as the glove or back side of the glove only, is placed. The glove may be placed and arranged on the support surface in a substantially flat, unfolded manner, such that the glove resembles the shape of the human hand if the hand were placed on the support surface palm-side down.

The support surface may be part of, or is operably connected to the load cell. The load cell is configured to measure a transferred impact force (pounds force, for example) resulting from the impact force applied to the glove. In one embodiment, multiple measurements may be taken. In such an embodiment, an average of the measurements at each location may be calculated to determine a transferred impact force.

In one embodiment, the transferred impact force may be compared to the baseline impact force and a percentage of impact resistance may be calculated as:

$$(F_{baseline} - F_{transferred})/F_{baseline} \qquad (1)$$

Where $F_{baseline}$ refers to the baseline transferred impact force in a glove with no protective material (e.g., padding), and $F_{transferred}$ refers to the measured transferred impact force in a glove having protective material, respectively. $F_{baseline}$ will be the substantially the same across all locations and regions on the glove. The $F_{transferred}$ value may be a value taken at particular location, an average of measured transferred impact forces in region, or an average of all measured transferred impact forces on the glove.

In one embodiment, the baseline impact force, i.e., the measured transferred impact with no protective material, is about 170 pounds force. An average of the impact forces measured across an entire back of the hand of the test surface may also be calculated by averaging the transferred impact force at all locations. The entire back of hand average may then be compared to the baseline impact force to determine an average percentage of impact resistance for the glove.

An impact resistance test method, according to the embodiments described herein, may be carried out as follows. An initial baseline test may be performed on a glove without protective material or padding. Here, the term "glove" may refer to only a back side of a glove, separated from the front or palm side, or a glove in its entirety. Alternatively, the test may be performed on a front side of the glove, separated from the back side. An impactor having a weight of one (1) lb is dropped onto the glove from a height of six inches to apply the impact force. A load cell measures the transferred impact force through the glove to obtain a baseline impact force value. According to one embodiment, this baseline value is approximately 170 lbs force.

A glove having protective material may be tested according to the methods described herein as well. The glove may be disposed on the support surface. The impactor, weighing one (1) pound, may then be dropped, under gravity, from six inches above the glove to apply the impact force. The transferred impact force may be measured by the load cell operatively connected to the support surface. The test may be repeated at multiple locations on the glove, for example, at the twelve locations shown in FIG. 1. In some embodiments, multiple tests may be performed at each location and the transferred impact forces may be averaged to determine an average transferred impact force.

The method further includes determining an impact resistance of the glove. According to one embodiment, determining the impact resistance of the glove includes comparing the transferred impact forces to the baseline impact force. In one embodiment, the transferred impact force at each glove location may be compared to the baseline impact force to determine a percentage impact resistance at each location. Alternatively, or in addition, the transferred impact forces may be averaged in regions of the glove to provide an average region transferred impact force. Alternatively, or in addition, all of the transferred impact forces may be averaged together to provide a single average transferred impact force for the glove (or back side of the glove, in one embodiment). Accordingly, the percentage of impact resistance may be determined at each location, region or entire glove by carrying out the calculations described above.

In one embodiment, the method may further include determining an impact protection cover factor at each region and/or over an entire surface of the glove. The cover factor refers to a percentage of area covered by the impact protection material, and may be calculated or measured for each region of the glove 100. An average of the cover factors at each region results in a single cover factor for the entire back of the glove area.

In the embodiments above, the initial baseline impact force determination may be omitted, and impact resistance may be expressed as the transferred impact force, rather than as a percentage of transferred impact force. In addition, a shaft to which the impactor may be attached can be monitored for residual friction and lubricated, if necessary, so that the applied impact force may be accurately controlled.

Figure 3A:
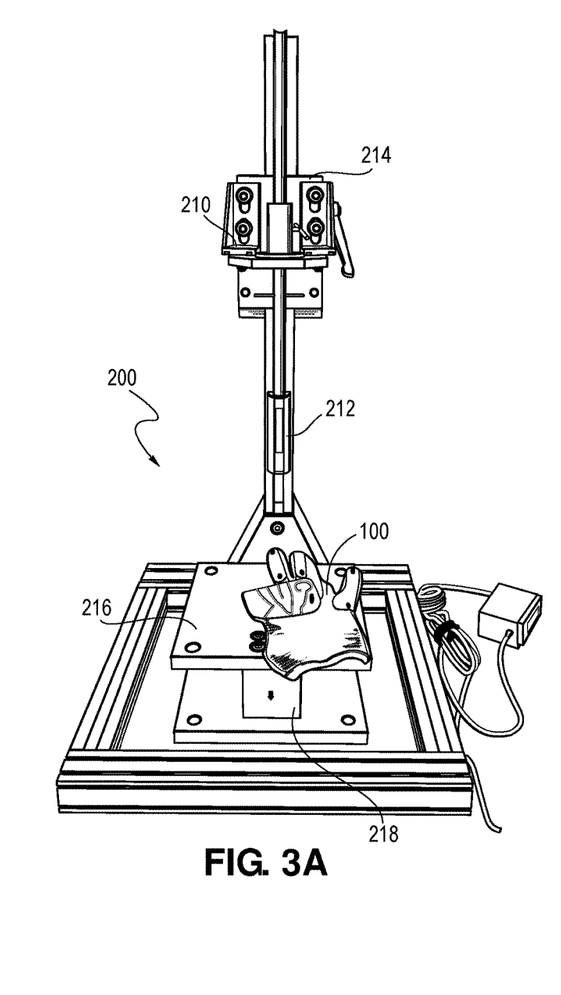
FIG. 3A shows an embodiment of the apparatus generally.
Figure 3B:
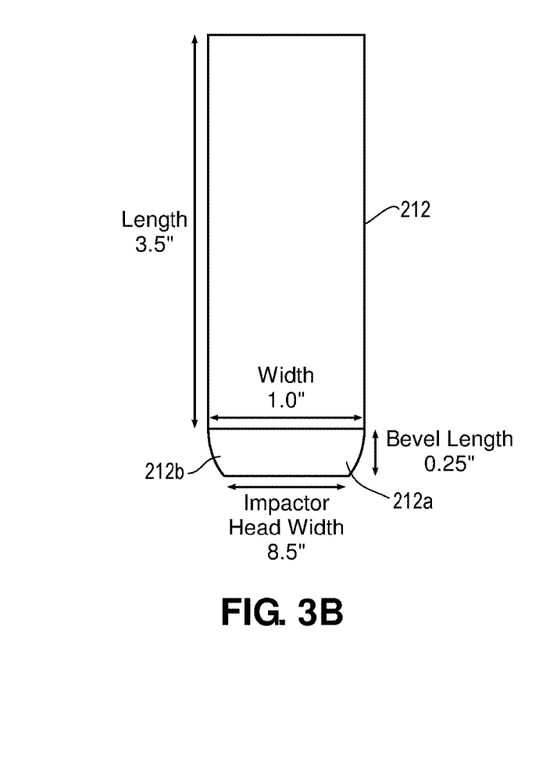
FIG. 3B shows an embodiment of the impactor.

FIGS. 3A and 3B show an example of an apparatus 200 for conducting the test methods described herein, according to one embodiment. Referring to FIG. 3A, the apparatus 200 includes, generally, a frame 210, an impactor 212, an impactor guide 214, a support surface 216, a load cell 218 and a control system 220. The frame 210, in general, support the impactor 212 and the impactor guide 214. In one embodiment the impactor 212 weighs approximately one pound and is configured to be held at a predetermined height above the support surface 216. The impactor 212 is also configured to be released from the predetermined to height to drop, under gravity, toward the support surface 216 to impart the impact force on the glove 100. The impactor is guided during movement, held in place by, and released by the impactor guide 214. The impactor guide 214 may include a drop tunnel to guide the impactor or a shaft of the impactor 212. In an embodiment, the impactor 212, shown in FIG. 3B is formed as a rod having a diameter of about 1.0 inches and a length of about 3.5 inches. The head 212a of the impactor has a bevel having a bevel length of about 0.25 inches that terminates in an impactor contact surface 212b having a width or diameter of about 0.5 inches and an area of about 0.79 in$^2$.

The support surface 216, according to one embodiment, is a substantially flat, plate-like surface on which the glove 100 may be disposed during the impact resistance test. The support surface 216 is operatively connected to a load cell 218, such that the load cell may measure an impact force transferred to the support surface 216 by the impactor 212. During a test according to the embodiments described herein, the impact force is transferred to the support surface 216 though the glove 100 and/or protective material that is being tested. In one embodiment, the support surface 216 and load cell 218 may be integrated as a single unit.

The load cell 218 may be connected to the control system 220 by way of an interface. In one embodiment, the interface may be a USB interface, such as a Loadstar DI-1000 USB Interface. However, other suitable interfaces are envisioned as well, including other wired interfaces or wireless interfaces.

The control system 220 may be implemented as a computer or other, similar processing device. The computer 220 is configured to receive the transferred impact force data from the load cell 218. The computer 220 includes a memory for storing program instructions and a processor for executing program instructions. In one embodiment, the computer includes a logging program, such as LoadVUE, for logging the transferred impact forces measured by the load cell 218. The computer 220 is configured to execute program instructions to carry out the calculations and determinations described in the embodiments above, and output and/or store the calculated or determined values.

Accordingly, the test method of one embodiment may be carried out as follows: check impactor guide 214 and/or shaft for additional sources of friction and oil if necessary; trim all palm areas 120 of the glove 100 so that all that remains is the back of glove areas 120 only; connect computer 220 to the load cell 218 interface; run load cell program; select a graph option on load cell program; "Tare All" before starting the test measurements; select "Start" to begin test; drop one pound weight/impactor onto back of glove 110; record transferred impact result in pounds force; select "Stop"; take three measurements at each desired region of the back of glove 110 including back of hand region R1, knuckle strap region R2, finger region R3 and thumb region R4; within each region, test three locations; after testing, take an average of transferred impact force each location, then each region, and finally the entire back of the glove 110; compare the transferred impact force results or average(s) to baseline of 170 pound force, and calculate a percentage of impact resistance; calculate or measure a cover factor for each region, and determine an average cover factor for the back of the hand; and calculate overall impact cover factor as percentage of total coverage.

Figure 4:
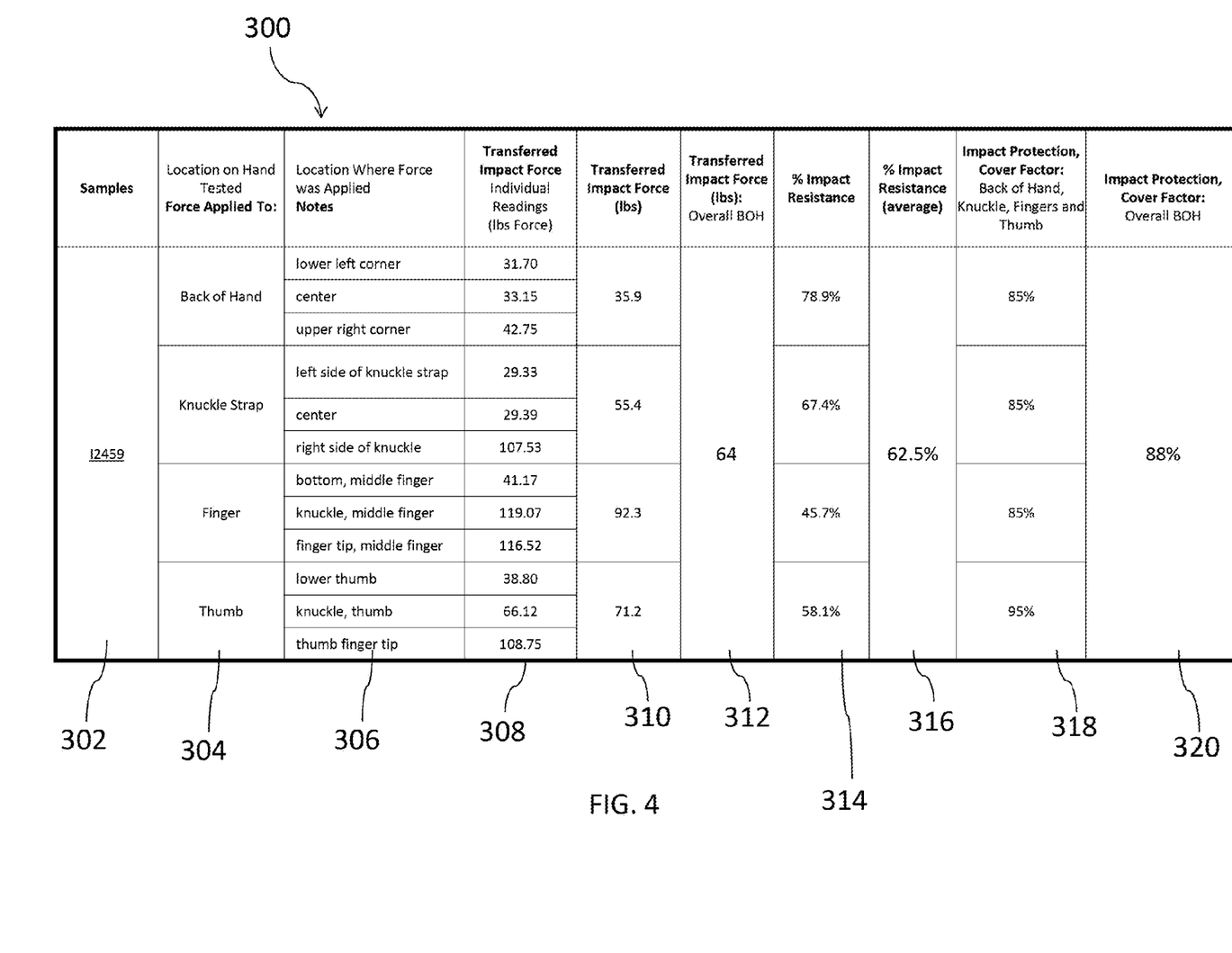
FIG. 4 is a table showing an example of test results from an impact resistance test on a glove, according to an embodiment described herein.

FIG. 4 is a table 300 showing test results from an impact resistance test carried out according to the embodiments described herein. Referring to FIG. 4, a particular sample or part number 302 upon which the test is conducted is stored. The impactor 212 may be dropped at one or more glove regions 304, and at one or more locations 306 within each glove region. In one embodiment, as shown in FIG. 4, the impactor 212 may be dropped onto the glove 100 at twelve different locations: lower left corner, center, and upper right corner on the back of hand region of the glove; left side of knuckle, center, and right side of knuckle on the knuckle strap region; bottom, knuckle, and finger tip of the middle finger region; and lower, knuckle, tip of the thumb region. The transferred impact force 308 may be measured by the load cell 218 at each location. The transferred impact forces for each location in a particular region, e.g., the back of the glove, the knuckle strap, the middle finger, the thumb, may be averaged based on the transferred impact forces at each location to obtain average transferred impact forces for each region 310. These region averages may be averaged together to determine an overall back of hand (BOH) or back of glove average transferred impact force 312.

Referring to still to FIG. 4, a region average impact resistance percentage 314 may be determined based on a comparison of the average region transferred impact force 310 to the baseline impact force, calculated as detailed above. The average region transferred impact forces 310 may then be averaged to obtain to overall back of hand or back of glove impact resistance average 316. An impact protection cover factor may also be determined for each region 318 and overall for the back of glove 320.

The calculations and determinations shown in table 300 may be carried out by the computer 200, and the table 300 may be generated and stored at the computer 200, and output by the computer 200 via suitable, known output devices, such as display screens, printing or in a desired file format.

Although the test method is described primarily with reference to back side of glove, it is understood that the methods described herein may be carried out on a front side of a glove as well. It is also understood that the test method described herein may be carried out on other impact resistant equipment such as protective foot wear and the like.

Accordingly, in the embodiments above, an impact resistance value or rating may be determined for any number of gloves or glove styles, and may be readily compared to impact resistance value or ratings of other gloves or glove styles that were tested according to the embodiments described herein. It will also be appreciated that the present method and apparatus can be used to test the impact protection of the fingers as well, whereas prior methods and devices could only be used to test impact protection of the back of the hand/glove.

It is understood that the features described with respect to any of the embodiments above may be implemented, used together with, or replace features described in any of the other embodiments above.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An impact resistance test method of a glove having a protective material, the method comprising:
   trimming a section of the glove having the protective material from the glove;
   applying an impact force, with an impactor, to the section of the glove at a plurality of locations;
   measuring, with a load cell, a transferred impact force transferred through section of the glove; and
   determining an impact resistance of the glove based on the measured transferred impact force,
   wherein the impactor has a predetermined weight and is dropped from a predetermined height to apply the impact force to the section of the glove.

2. The impact resistance test method of claim 1, wherein the predetermined weight is one pound.

3. The impact resistance test method of claim 1, wherein the predetermined height is six inches.

4. An impact resistance test method of a glove having a protective material, the method comprising:
   applying an impact force, with an impactor, to the glove at a plurality of locations on a section of the glove;
   measuring, with a load cell, a transferred impact force transferred through section of the glove; and
   determining an impact resistance of the glove based on the measured transferred impact force,
   wherein the impactor has a predetermined weight and is dropped from a predetermined height to apply the impact force to the section of the glove,
   the impact resistance test method further comprising determining a baseline impact force, wherein determining the baseline impact force comprises:
   applying the impact force, with the impactor, to a section of a baseline glove that is free of the protective material; and
   measuring, with the load cell, a baseline transferred impact force transferred through section of the baseline glove free of protective material.

5. The impact resistance test method of claim 4, wherein the step of determining an impact resistance of the glove further comprises:
   comparing a measured transferred impact force through the section of the glove to the baseline impact force; and
   determining a percentage of impact resistance of the glove based on the comparison of the measured transferred impact force and the baseline impact force.

6. The impact resistance test method of claim 4, wherein applying the impact force at a plurality of locations includes applying the impact force at a plurality of regions on the section of the glove, each region comprising one of more locations of the plurality of locations.

7. The impact resistance test method of claim 6, wherein determining the impact resistance of the glove further comprises averaging the measured transferred impact force at each location within respective regions to obtain an average transferred impact force for each region.

8. The impact resistance test method of claim 7, wherein determining the impact resistance of the glove further comprises averaging the averaged transferred impact forces for each region to obtain an average transferred impact force for the glove.

9. The impact resistance test method of claim 8, wherein determining the impact resistance of the glove further includes determining a percentage of impact resistance of the glove based on a comparison of the baseline impact force to the average transferred impact force for the glove.

10. An impact resistance test method of a glove having a protective material, the method comprising:
    applying an impact force, with an impactor, to the glove at a plurality of locations on a section of the glove;
    measuring, with a load cell, a transferred impact force transferred through section of the glove;
    determining an impact resistance of the glove based on the measured transferred impact force; and
    determining an impact protection cover factor,
    wherein the impactor has a predetermined weight and is dropped from a predetermined height to apply the impact force to the section of the glove.

11. An impact resistance test method of a glove having a protective material, the method comprising:
    applying an impact force, with an impactor, to the glove at a plurality of locations on a section of the glove;
    measuring, with a load cell, a transferred impact force transferred through section of the glove; and
    determining an impact resistance of the glove based on the measured transferred impact force,
    wherein the impactor has a predetermined weight and is dropped from a predetermined height to apply the impact force to the section of the glove, and
    wherein the section of the glove is a back side of the glove that has been separated from a front side of the glove.

12. An apparatus for performing an impact resistance test method on a glove; the apparatus comprising:
    a frame;
    an impactor configured for vertical movement to impact the glove;

an impactor guide configured to hold the impactor at a first position, release the impactor, and guide the impactor during vertical movement;
a support surface configured to support the glove, wherein the support surface is substantially flat;
a load cell operably connected to the support surface, the load cell configured to measure a transferred impact force transferred through the glove; and
a control system operably and communicably connected to the load cell, the control system configured to receive the measured transferred impact force from the load cell and determine an impact resistance of the glove based on the measured transferred impact force and a baseline impact transferred force.

* * * * *